(12) United States Patent
Mitchell

(10) Patent No.: US 6,386,145 B1
(45) Date of Patent: May 14, 2002

(54) PROCESS FOR CURING DISEASES IN CULTURED FISH

(75) Inventor: Charles A. Mitchell, Greenville, MS (US)

(73) Assignee: B. L. Mitchell, Inc., Leland, MS (US)

( * ) Notice: Subject to any disclaimer, the term of this patent is extended or adjusted under 35 U.S.C. 154(b) by 0 days.

(21) Appl. No.: 09/515,764

(22) Filed: Mar. 1, 2000

(51) Int. Cl.$^7$ .............................................. A01K 61/00
(52) U.S. Cl. ..................................................... 119/215
(58) Field of Search ......................................... 119/215

(56) References Cited

U.S. PATENT DOCUMENTS

| | | | | |
|---|---|---|---|---|
| 4,219,543 A | * | 8/1980 | Hartmann et al. | 424/89 |
| 4,418,648 A | * | 12/1983 | Lightner | 119/2 |
| 4,826,842 A | * | 5/1989 | Mehlhorn et al. | 514/241 |
| 5,188,832 A | * | 2/1993 | Mehlhorn et al. | 424/405 |
| 6,054,454 A | * | 4/2000 | Schmid et al. | 514/229.2 |
| 6,160,023 A | * | 12/2000 | Braidwood | 514/727 |

OTHER PUBLICATIONS

Rainbow Trout (*Oncorhynchus mykiss*) Blood During Exposure to Chloramine T, Paramtoluenesulphonamide and hypochlorite by M.D. Powell & S.F. Perry Feb. 21, 1995 ©1996.

Kinetics and Mechanism of Osmium (VIII) Catalyzed Oxidation of Propane 1,3—Diol by N,–Chloro–P–Toluene Sulfonamide (Chloramine T) in Aqueous Alkaine Medium by Gupa et al 1998.

1–3 DiPulay Cycloaddition of Dipolar Reagents to Bifunctional Olefins in the Presence of Chloramine T By Padmavathi et al 1999.

Isolation and Characterization of Chloramine T Metabolites in Rainbow Trout after use Pattern Treatment wi Ring ul–$^{14}$ Chloramine T Study No CAP–93–00057 Dec. 1994 By Dawson et al.

Micro–organisms against which Halamid has proved active by Akzo Nobel.

Oxidation of Methionine Residues in Equine Growth Hormone By Chloramine T By Minajlovic et al Jun. 20, 1993.

Liquid Chromatographic Determination of para Toluenesulfonamide in Edible Fillet Tissues from Three Species of Fish By J.R. Meinertz, et al. Apr. 6, 1999.

Efficacy of Chloramine–T for Control of Mortality Associated with Proliferative Gill Disease and Columnaris in Channel Catfish Protocol 10–752.

\* cited by examiner

*Primary Examiner*—Charles T. Jordan
*Assistant Examiner*—Kimberly S. Smith
(74) *Attorney, Agent, or Firm*—Donald R. Bahr

(57) ABSTRACT

This invention relates to a process for disease control in fish farming and more particularly, to a process whereby proliferative gill disease and other diseases and infections are eliminated by the treatment of a fish rearing pond or tank with low concentrations of Chloramine-T. The Chloramine-T is applied to the pond or tank and allowed to remain in the tank or pond until it breaks down. The concentration of the Chloramine-T can be from about 2 to about 3 PPM.

19 Claims, No Drawings

PROCESS FOR CURING DISEASES IN CULTURED FISH

FIELD OF THE INVENTION

This invention is concerned with the control of gill diseases in fish, more particularly with the control of these diseases in a cultured fish farming environment. In accordance with this invention a wide variety of fish gill diseases can be controlled or cured. The process of this invention comprises adding Chloramine-T to the aqueous environment which contains the diseased fish so as to achieve a specific but relatively low concentration of Chloramine-T.

BACKGROUND OF THE INVENTION

The use of Chloramine-T for curing diseases in fish is decades old, in the most common situation in the prior art diseased fish are exposed to solutions having a relatively high concentrations of Chloramine-T for a short period of time.

In the past when Chloramine-T was used for aquatic disease control diseased fish were exposed to a solution of Chloramine-T at concentrations in excess of 10 parts per million (ppm). These prior art exposures were effected in raceways or holding tanks for periods of time of from 10 to 20 minutes. After exposure to the Chloramine-T the fish were returned to rearing ponds. In the present invention the diseased fish are treated in their rearing ponds, thereby eliminating the trouble and expense of moving the diseased fish from their rearing ponds to holding tanks or raceways and then returning the fish to their rearing pond.

As is mentioned above to some degree the use of Chloramine-T for aquatic disease control is known in its prior art however the prior art treatment process is inherently different from the process of this invention.

With the process of this invention it is possible to control or cure proliferative gill diseases PGD which commonly afflicts catfish, which diseases are caused by a wide variety of pathogens. In its broadest terms, this invention relates to the utilization of a particular low concentration Chloramine-T solution, which kills the pathogens which are responsible for the PGD and thereby allow the fish to recover.

BRIEF DESCRIPTION OF THE INVENTION

Gill diseases have been a problem which man has addressed since the very beginning of aqua culture. These diseases can result in substantial or total fish loss in a particular rearing pond. Gill diseases are a common problem in fish aqua culture, these diseases being caused by crowded conditions which are necessary in order to make fish aqua culture practical. The susceptibility of fish to gill disease, in an aqua culture environment may be further enhanced by inadequate nutrition which leaves the fish in a weakened condition. With this invention proliferative gill disease (PGD) is easily controlled. PGD is a serious malady of intensively cultured fish, particularly young catfish. If it is not diagnosed and treated early, thousands of fish may die within a short period. Affected fish stop feeding, swim near the surface, and face into the current. Microscopically, gill epithelium is hyperplastic and covered with masses of long, thin gram-negative bacteria. Although death is caused by damage from a massive infection of the gills, stressors associated with intensive culture, such as crowding and low concentrations of dissolved oxygen, predispose fish to infection. Neither the stressors involved nor their modes of action are fully understood.

The subject invention is concerned with a process whereby a wide variety of PGD can be cured or controlled by use of the active chlorine in Chloramine-T to destroy the pathogens which are responsible for PGD.

In the preferred embodiment, fish which are showing signs of PGD are treated by applying Chloramine-T to the water in the rearing pond at a predetermined concentration. Using the process of this invention the diseased fish are cured because the active chlorine moiety destroys the pathogens which are responsible for the PGD. The water in the rearing pond must contain Chloramine-T in the correct concentration, as too much Chloramine-T will kill the weakened diseased fish and too little Chloramine-T will be ineffective. In other words in order to control PGD the Chloramine-T must be used at the correct concentration.

DESCRIPTION OF THE PREFERRED EMBODIMENT

In accordance with the above discussion this invention is concerned with a process for controlling or curing fish which are from suffering PGD. PGD is a term used to refer to a plurality of diseases, which are caused by exposure of the fish to gamma negative bacteria, myxobacteria, alromonads and pseudomonods. PGD results from crowding in the ponds or tanks which are used to contain the fish. Once started a disease can spread rapidly causing the loss of millions of fish as may be contained in a tank or pond. In the subject invention it is not necessary to remove the diseased fish to a separate environment for treatment, instead the tank or pond which contains the diseased fish is treated. While Chloramine-T has been used in the past to treat fish which are effected with PGD, in the prior art the fish were removed to a separate environment and treated for a short period of time in a separate holding tank or raceway.

In these prior art treatment processes a separate holding tank is prepared, such that the concentration of Chloramine-T is between 10 and 25 ppm.

Fish suffering from PGD were placed in the tank for a period of time of from about 10 to 20 minutes. The fish were then removed from the holding tank and returned to their respective tank or pond.

Another prior art process requires that the diseased fish be placed in a raceway wherein water is running through this raceway and a concentrated solution of Chloramine-T is fed into the raceway in order that the concentration of Chloramine-T in the raceway is between 10 and 20 ppm, and the fish are in the raceway for between 10 and 20 minutes, whereupon the fish are returned to their respective tank or holding pond.

These prior art treatment processes are disadvantageous in that the diseased fish are exposed to relatively high concentrations of Chloramine-T. In view of this exposure some of the meat of the fish may be contaminated with Chloramine-T, as a result of this contamination the meat becomes unmarketable. A further disadvantage of these prior art processes is the trouble and expense of moving the diseased fish from one environment to another.

Fish which are diseased with PGD tend to stop eating, lose their orientation and float on their side. If action is not taken immediately the whole population of the tank or pond can be dead within 24 to 48 hours.

In contrast to the prior art process described above in accordance with this invention there is no need to remove the fish to a separate treatment environment. Instead in accordance with the process of this invention, the tank or pond in which the diseased fish are contained in treated with Chloramine-T, wherein the concentration of Chloramine-T is between 2 and 3 ppm. If the concentration of Chloramine-T is allowed to exceed 3 ppm the weakened fish will die as a result of the long term exposure to Chloramine-T. In contrast if the concentration of the Chloramine-T is less than 2 ppm the treatment is ineffective and the fish will not be cured of PGD.

The broad range for treatment in accordance with the process, is a Chloramine-T concentration of from about 2 to about 3 ppm, a more preferred concentration for the Chloramine-T for use in this invention is between 2.15 and 2.75 ppm with a preferred concentration being 2.5 ppm.

In order to effect these concentrations in the tank or pond where the diseased fish are contained the concentrated solution of Chloramine-T is prepared for using the correct amount of Chloramine-T for the volume of water which is contained in the tank or pond where the diseased fish reside. This concentrated solution is then spread evenly over the surface of the pond or tank via the use of a chemical boat. In order to aid mixing aeration equipment is run one hour before the application and 35 hours after the application.

As an alternative procedure powdered Chloramine-T may be spread evenly over the surface of the pond.

It is preferable that the Chloramine-T be added to the tank or pond during daylight in order to allow the thermal currents created by sunlight and wind to facilitate the mixing of the Chloramine-T with the water of the pond or tank. Further the use of aeration equipment as described above aids in the mixing.

For example in order to achieve a concentration of 2 ppm of Chloramine-T 5.38 pounds of Chloramine-T is added per acre foot of water as may be contained in the tank or pond, containing the diseased fish.

The process of this invention may be used to treat a wide variety of fish such as trout, salmon, tilapia, flounder and catfish. This invention is particularly suited for the treatment of catfish.

The process of this invention can be used to treat fish from 2" in length on up.

In addition to being an effective treatment for PGD the process of this invention is effective in treating diseased fish for other maladies such as external columnaris, gill flukes, bacterial infection ESC, and parasites.

Upon treatment the death rate of the diseased fish decreases over the first three days and essentially stops after three days.

Most fish ponds or tanks are, what is referred to in the trade, "organic". That is the water in which the fish are being reared have a high particulate content of organic material. This organic material comes from two principal sources these being fecal material and fish feed. This organic material is referred to as the bio load.

This organic material is detrimental to the concentration of Chloramine-T in the pond or tank as the Chloramine-T goes into solution it produces a Cl+ moeity. It is this Cl+ moeity which is active in treating the fish diseases as discussed above. This Cl+ moeity is very active and readily reacts with the bio load as is contained in the tank or pond. If this reaction occurs there is less Cl+ to fiction as a disease control agent. Further the Cl+ moeity is degraded by sunlight, dissolved oxygen, and ultra violet light.

The rate of the above discussed reactions is further controlled by the temperature of the water in the holding tank or pond.

In view of the above discussed reactions and variables, one skilled in the art recognizes that the concentration of the dissolved Chloramine-T and particular the Cl+ moeity may be monitored and if the concentration drops below the range as specified above additional Chloramine-T may be added to the pond or tank.

In still another embodiment of this invention low concentrations of Chloramine-T are used on a continuous basis to prevent PGD from infecting a healthy population of fish that are being raised. In this embodiment low concentrations of Chloramine-T are maintained in the fish holding tank or pond, on a continuous basis. In this embodiment concentrations of Chloramine-T are continuously maintained at from about 2 to about 3 ppm., a more preferred range is from about 2.00 to about 2.40 ppm with a most preferred concentration being 2.15 ppm.

In order to prevent contamination of the fish tissue with Chloramine-T it is recommended that all treatment of the fish with Chloramine-T be discontinued at least ninety days prior to harvest.

Chloramine-T is a common trivial name used to describe a variety of compounds which are based on N-Sodium, N-chloro-para-toluenesulfonamide. The preferred Chloramine-T for use in this invention is a tri-hydrated sodium salt having the following formula.

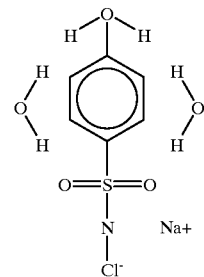

While Chloramine-T is the preferred source of the Cl+ moeity in accordance with this invention another source for a suitable Cl+ moeity is Chloramine-B.

As is stated above the component of Chloramine-T which is responsible for the disease control is the Cl+ moeity which is produced when Chloramine-T goes into solution. One skilled in the art recognizes that there are other sources for the Cl+ moeity i.e. common bleach. While the mechanics of the process are not fully understood other sources of Cl+ moeity such as bleach are not suitable for use in accordance with this invention. If bleach is added to the ponds or tanks which contain diseased fish, in concentrations sufficient to kill the pathogens which are responsible for PGD, the pathogens are killed however the fish are likewise killed. In view of this fact bleach is not a suitable source for the Cl+ moeity for use in this invention.

The Cl+ moeity which is produced by bleach is much more ionic when compared to the cation produced by Chloramine-T. That is when compared to the Cl+ moeity produced by bleach the Cl+ moeity produced by Chloramine-T is much more covalent. As a result of this covalence the side effects produced by the Cl+ moeity produced by Chloramine-T are not as severe as those produced by other sources and in particular by bleach. Further when compared to bleach the Cl+ moeity produced by Chloramine-T is much more stable and it has a higher Cl+ activity. Chloramine-T is further advantageous in that the residual molecule remaining after the Cl+ moeity is removed is non toxic to fish. While not fully understood it is felt that the advantageous properties of Chloramine-T, in the subject environment, result from the nature of the Cl to N bond in Chloramine-T.

EXAMPLES

The present invention is illustrated by the following Examples which are not to be constructed as limiting the invention to their details.

1. A pond of 17 acres, 4.5 feet deep holding approximately 2 million catfish contained approximately 76.5 acre feet of water. The catfish were 2 to 4 inches in length. Some of the fish exhibited unusual behavior which reflected the symptoms of PGD. Upon examination the whole fish population was diagnosed as having PGD in various stages with some of the fish dying. 411.57 pounds of Chloramine-T was dissolved in 50 gallons of water contained in a tank on a chemical boat, as the boat moved over the pond the the Chloramine-T was applied evenly over the surface of the pond. This application produced an effective concentrations of Chloramine-T of 2 ppm, 24 hours after application of the Chloramine-T to the pond the death rate of the fish substantially decreased . After 48 hours the death rate had further decreased. After 72 hours the death of fish essentially stopped and upon examination of the fish population it was observed that the PGD was in remission. A further examination of the fish population after 96 hours indicated that the fish population was free of PGD.

2. A pond of 17 acres, 4.5 feet deep holding approximately 1 million catfish contained approximately 76.5 acre feet of water. The catfish were 6 to 9 inches in length. Some of the fish exhibited unusual behavior which reflected the symptoms of PGD. Upon examination the whole fish population was diagnosed as having PGD in various stages with some of the fish dying. 411.57 pounds of Chloramine-T was dissolved in 50 gallons of water and sprayed evenly over the surface of the pond. The application process was as described in Example 1. This application produced as effective concentrations of Chloramine-T being 2 ppm, 24 hours after application of the Chloramine-T to the pond the death rate of the fish substantially decreased. After 48 hours the death rate had further decreased. After 72 hours the death of fish essentially stopped and upon examination of the fish population it was observed that the PGD was in remission. A further examination of the fish population after 96 hours indicated that the fish population was free of PGD.

3. A pond 17 acres 4.5 feet deep holding approximately 125,000 catfish contained approximately 76.5 acre feet of water. The catfish were 1 to 1.25 pounds in weight. Some of the fish exhibited unusual behavior which reflected the symptoms of PGD. Upon examination the whole fish population was diagnosed as having PGD in various stages with some of the fish dying. 411.57 pounds of Chloramine-T was dissolved in 50 gallons of water and sprayed evenly over the surface of the pond. The application process was as described in Example 1. This application produced an effective concentrations of Chloramine-T of 2 ppm, 24 hours after application of the Chloramine-T to the pond the death rate of the fish substantially decreased. After 48 hours the death rate had further decreased. After 72 hours the death of fish essentially stopped and upon examination of the fish population it was observed that the PGD was in remission. A further examination of the fish population after 96 hours indicated that the fish population was free of PGD.

4. A pond of 17 acres 4.5 feet deep holding approximately 700,000 catfish contained approximately 76.5 acre feet of water. The catfish were 8 to 11 inches in length. Some of the fish exhibited unusual behavior which reflected the symptoms of PGD. Upon examination the whole fish population was diagnosed as having PGD in various stages with some of the fish dying. 411.57 pounds of Chloramine-T were dissolved in 50 gallons of water and sprayed evenly over the surface of the pond. The application process was as described in Example 1. This application produced an effective concentrations of Chloramine-T being 2 ppm 24 hours after application of the Chloramine-T to the pond the death rate of the fish substantially decreased. After 48 hours the death rate had further decreased. After 72 hours the death of fish essentially stopped and upon examination of the fish population it was observed that the PGD was in remission. A further examination of the fish population after 96 hours indicated that the fish population was free of PGD.

5. A pond 17 acres 4.5 feet deep holding approximately 700,000 catfish contained approximately 76.5 acre feet of water. The catfish were 8 to 11 inches in length.

Some of the fish exhibited unusual behavior which reflected the symptoms of PGD.

Upon examination the whole fish population was diagnosed as having PGD in various stages with some of the fish dying. 309 pounds of Chloramine-T as dissolved in 50 gallons of water and sprayed evenly over the surface of the pond. The application process was as described in Example 1. This application produced as effective concentrations of Chloramine-T of 1.5 ppm, 24 hours after application of the Chloramine-T to the pond there was no decrease. in the death rate of the fish.

After 48 hours the death rate was not decreased. After 72 hours the death of fish continued and upon examination of the fish population it was observed that the PGD continued unabated. A further examination of the fish population after 96 hours indicated that the fish population continued to die and be afflicted with PGD.

6. A pond of 12 acres 4 feet deep holding approximately 450,000 catfish contained approximately 48 acre feet of water. The catfish were 8 to 11 inches in length. Some of the fish exhibited unusual behavior which reflected the symptoms of PGD. Upon examination the whole fish population was diagnosed as having PGD in various stages with some of the fish dying. 387 pounds of Chloramine-T was dissolved in 50 gallons of water and sprayed evenly over the surface of the pond. The application process was as described in Example 1. This application produced an effective concentration of Chloramine-T of 1.5 ppm, 24 hours after application of the Chloramine-T to the pond all of the fish were dead.

In summary, the data of Examples 1 through 6 demonstrates that by use of the Chloramine-T in accordance with the process of the subject invention, eliminates PGD in, diseased catfish and that concentrations of less than 2 ppm are ineffective in controlling PGD and that concentrations of more than 3 ppm kill the diseased catfish.

The foregoing constitutes a description of various features of a preferred embodiment. Many changes to the preferred embodiment are possible without departing from the spirit and scope of the invention. Therefore, the scope of this invention should be determined with reference not to the preferred embodiments but to the following claims.

What is claimed is:

1. A process for treating a cultured fish population contained in a water environment for various maladies which comprises the steps of:
   a. observing the maladies in the fish population,
   b. allowing the fish population to remain in the environment where the maladies were observed,
   c. adding an effective amount of Chloramine-T to the water environment so as to achieve a Chloramine-T concentration of less than 3 ppm, d. allowing the cultured fish to remain in water environment so treated wherein the concentration of Chloramine-T is maintained at less than 3 ppm, e. discontinuing all treatment with Chloramine-T at least ninety days prior to harvest.

2. The process of claim 1 wherein the concentration of the Chloramine-T is from about 2 to about 3 ppm.

3. The process of claim 2 wherein the fish being treated are catfish which are afflicted with proliferative gill disease.

4. The process of claim 1 wherein the concentration of Chloramine-T is about 2.15 ppm.

5. The process of claim 4 wherein the fish being treated are catfish which are afflicted with proliferative gill disease.

6. The process of claim 1 wherein the concentration of Chloramine-T is from about 2 to about 3 ppm.

7. The process of claim 6 wherein the fish being treated are catfish which are afflicted with proliferative gill disease.

8. The process of claim 1 wherein the concentration of Chloramine-T is 2.00 ppm.

9. The process of claim 8 wherein the fish being treated are catfish which are afflicted with proliferative gill disease.

10. The process of claim 1 wherein the degration of Chloramine-T is monitored and additional Chloramine-T is added in order to maintain an effective amount of Chloramine-T.

11. The process of claim 10 wherein the fish being treated are catfish which are afflicted with proliferative gill disease.

12. The process of claim 1 wherein the fish being treated are catfish which are afflicted with proliferative gill disease.

13. A process for preventing the affliction of cultured fish, in a water environment, with various maladies by maintaining an effective concentration of Chloramine-T in said water environment, wherein said concentration is less than 3 ppm.

14. The process of claim 2 wherein the concentration of Chloramine-T is from about 2.20 to about 2.40 ppm.

15. The process of claim 14 wherein the fish being treated are catfish which are afflicted with proliferative gill disease.

16. The process of claim 13 wherein the concentration of Chloramine-T is 2.35 ppm.

17. The process of claim 16 wherein the fish being treated are catfish which are afflicted with proliferative gill disease.

18. The process of claim 13 wherein the degration of Chloramine-T is monitored and additional Chloramine-T is added in order to maintain an effective amount of Chloramine-T.

19. The process of claim 13 wherein the fish being treated are catfish which are afflicted with proliferative gill disease.

* * * * *